(12) United States Patent
Barak et al.

(10) Patent No.: US 10,018,574 B2
(45) Date of Patent: Jul. 10, 2018

(54) OPTICAL METHOD AND SYSTEM FOR DEFECTS DETECTION IN THREE-DIMENSIONAL STRUCTURES

(71) Applicant: NOVA MEASURING INSTRUMENTS LTD., Rehovot (IL)

(72) Inventors: Gilad Barak, Rehovot (IL); Elad Dotan, Talmei Yehiel (IL); Alon Belleli, Gedera (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 15/325,877

(22) PCT Filed: Jul. 14, 2015

(86) PCT No.: PCT/IL2015/050729
§ 371 (c)(1),
(2) Date: Jan. 12, 2017

(87) PCT Pub. No.: WO2016/009433
PCT Pub. Date: Jan. 21, 2016

(65) Prior Publication Data
US 2017/0138868 A1 May 18, 2017

Related U.S. Application Data

(60) Provisional application No. 62/024,018, filed on Jul. 14, 2014.

(51) Int. Cl.
*G01N 21/956* (2006.01)
*G01N 21/88* (2006.01)
(Continued)

(52) U.S. Cl.
CPC ... *G01N 21/95692* (2013.01); *G01N 21/8806* (2013.01); *G01N 21/8851* (2013.01);
(Continued)

(58) Field of Classification Search
CPC ......... G01N 21/95692; G01N 21/9501; G01N 21/95607; G01N 21/8806; G01N 21/8851; G06T 7/0008; G06T 7/001
See application file for complete search history.

(56) References Cited

U.S. PATENT DOCUMENTS 8,848,185 B2 9/2014 Barak et al.
2003/0099392 A1 5/2003 Levin et al.
(Continued)

FOREIGN PATENT DOCUMENTS

WO 013121423 A1 8/2013
WO 14006614 A1 1/2014

*Primary Examiner* — Sang Nguyen
(74) *Attorney, Agent, or Firm* — Browdy and Neimark, PLLC

(57) ABSTRACT

An inspection system and method are presented for inspecting structures having a pattern formed by an array of elongated grooves having high aspect-ratio geometry, such as semiconductor wafers formed with vias. The inspection system comprises an imaging system and a control unit. The imaging system is configured and operable for imaging the structure with a dark-field imaging scheme and generating a dark-field image. The control unit comprises an analyzer module for analyzing pixels brightness in the dark-field image for identifying a defective groove, being a groove characterized by pixels brightness in the dark-field image lower than nominal brightness by a predetermined factor.

25 Claims, 3 Drawing Sheets a b

(51) Int. Cl.
    *G01N 21/95*   (2006.01)
    *G06T 7/00*    (2017.01)

(52) U.S. Cl.
    CPC ... *G01N 21/9501* (2013.01); *G01N 21/95607* (2013.01); *G06T 7/001* (2013.01); *G06T 7/0008* (2013.01); *G01N 2021/8825* (2013.01); *G01N 2021/8848* (2013.01); *G06T 2207/10056* (2013.01); *G06T 2207/30148* (2013.01)

(56) References Cited

U.S. PATENT DOCUMENTS

| | | | |
|---|---|---|---|
| 2004/0196453 A1* | 10/2004 | Some | G01N 25/72 356/237.1 |
| 2005/0110988 A1 | 5/2005 | Nishiyama et al. | |
| 2006/0038987 A1 | 2/2006 | Meada et al. | |
| 2008/0015802 A1* | 1/2008 | Urano | G01N 21/4738 702/81 |
| 2008/0292176 A1* | 11/2008 | Sakai | G06T 7/001 382/144 |
| 2012/0207382 A1* | 8/2012 | Maeda | G06K 9/00557 382/149 |
| 2013/0343632 A1* | 12/2013 | Urano | G06T 7/001 382/149 |
| 2015/0369752 A1* | 12/2015 | Honda | G01N 21/8851 356/237.2 |

\* cited by examiner

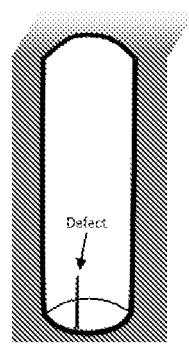
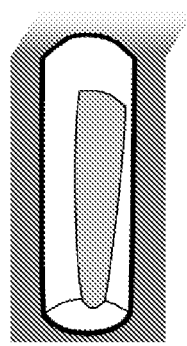
FIG. 1A      FIG. 1B
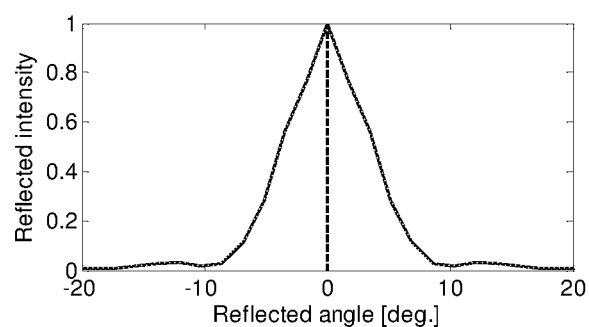
FIG. 1C

OPTICAL METHOD AND SYSTEM FOR DEFECTS DETECTION IN THREE-DIMENSIONAL STRUCTURES

TECHNOLOGICAL FIELD

This invention is generally in the field of optical inspection techniques, and relates to an optical method and system for detecting defects in three-dimensional structures, specifically in semiconductor wafers formed with vias.

BACKGROUND

As semiconductor technology progresses, shrinking device dimensions has become an increasingly complex task. One approach to overcome these difficulties is the vertical integration of multiple semiconductor chips, allowing either larger number of devices per unit (e.g. in memory applications) or the integration of chips providing different functionality, allowing better performance of a hybrid system (e.g. sensor, processor and memory). One method for vertical integration is based on Through Silicon Via (TSV), in which conducting pillars are formed within the silicon substrate, to be later used for contacting successive chips. TSV technology provides the electrical interconnect between the components in different layers, and also provides mechanical support. In TSV technology, a via is fabricated in a silicon chip with different active integrated circuit devices or other devices fabricated by a semiconductor process, and the via is filled with metal such as Cu, Au, W, solders, or a highly-doped semiconductor material such as polysilicon. Multiple components provided with such vias are then stacked and bonded together.

One critical step in the TSV process is the via formation, in which a pattern of contacts is etched into the silicon. In this process, defects in the TSV might be produced. In order to maintain the required via quality, it is essential to detect defective vias.

In WO 2014/006614, assigned to the assignee of the present invention, a method and system were presented for use in inspection of via containing structures. According to this technique, measured data indicative of a spectral response of a via-containing region of a structure under measurements is processed, and, upon identifying a change in at least one parameter of the spectral response with respect to a spectral signature of the via-containing region, output data is generated indicative of a possible defect at an inner surface of the via.

GENERAL DESCRIPTION

There is a need in the art for a novel inspection technique for detecting defective features in a patterned structure, where the features to be inspected are narrow and deep (high-aspect ratio) grooves, such as vias in a semiconductor wafers. The inspection technique can for example be aimed at monitoring/controlling a patterning process, such as via fabrication process, e.g. a TSV process.

The high aspect ratio grooves that can be effectively inspected by the technique of the invention are grooves having a high aspect ratio geometry, i.e. a ratio between the length/depth of the groove and any one or both of its lateral dimensions (e.g., diameter). It should thus be understood that the term "groove" used herein should be interpreted broadly, covering any recess or hole or via whose length/depth extends downwards from a surface/layer and whose cross-section may be of any geometry (circular, polygonal) provided that a ratio between the length and any or both of the cross-sectional dimensions is high, e.g. at least 6. Considering such grooves or vias used in semiconductor structures, these may be through vias, blind and buried vias, etc. These types of vias are well known in the field of semiconductor devices, and therefore need not be described in details. Considering an example of TSVs, typical cross section sizes of the via (via diameters) are in the range of 1-50 µm, and depths are up to 200 µm, providing aspect ratios up to 20:1. The present invention provides such an easy-to-implement, fast, effective and strongly reliable method and system for use in monitoring large production of semiconductor wafers utilizing the TSV process.

Generally, the technique of the invention provides for automatic inspection of patterned structures to identify defective structures and possibly also the defective sites in such structures. This may be inspection of the structures while progressing on a production line (so called "on-line inspection") enabling further verification of the detected defects, or automatic inspection by a stand alone inspection system.

It should be noted that although the description below refers specifically to wafers with vias, e.g. TSVs, the principles of the invention can be used for defect detection in various other elongated, high aspect ratio (i.e. narrow) grooves created by any technology (not necessarily etching a silicon layer) in any structure. The vias/grooves that can be inspected for defects by the technique of the invention are high aspect ratio grooves, namely deep and narrow grooves, TSVs being a specific but not limiting example of such type of grooves.

TSVs are created by deep silicon etch, yielding a vertical hole in the silicon. It is important to detect any defect in a via, because defects might cause faulty coverage and/or filling of the via in later fabrication steps (lead to improper coating and deposition processes in the next fabrication steps), as well as might cause electrical shorts between the via (filled with Cu) and the substrate, eventually causing the entire device to malfunction. Detection of such defects is of detrimental importance for the future functionality of a chip, and thus of significant industrial interest.

One important defect form that could appear, as shown in FIG. 1A, is the formation of sharp spikes at the bottom or on the TSV walls. Another defect type that can be found in TSV, is that a a large portion of the TSV is not etched, or alternatively a 'curtain'-like structure remains after the etch process. This is shown in FIG. 1B. Several other mechanisms of TSV defectivity are known in the literature, each arising from different deviations of the fabrication process from its intended process window.

Generally, these defects will not extend to the TSV opening (at the wafer surface). The high aspect ratio (reaching >1:10), and small typical cross-sectional dimension/diameter (a few micrometers), prevent the use of standard imaging techniques to identify these buried defects.

Moreover, it is desired to enable defect detection by automatic (optical) inspection (AOI) of patterned structure, to enable automatic classification and sorting the structures being inspected into "normal" and "defective" structures. To this end, the technique of the present invention utilizes an imaging technique for imaging a sample (a region/site of the sample) under inspection with a relatively large field of view i.e., a field of view covering multiple features (grooves/vias) of the pattern, and processing the image (picture). The imaging is performed using dark-field scheme(s). The pixels brightness in the data indicative of the dark-field image is analyzed, and upon identifying that brightness of pixels corresponding to at least one of these features in the dark-field image as compared to nominal brightness (e.g. that of other of such features and/or reference (golden, non-defective) dark-field image and/or bright-field image data), generating output data indicative of existence of at least one defective feature in the measurement site. In some embodiments, the defective feature is that characterized by the dark-field image brightness lower than that of the other features or that of the golden dark-field image. This is typically lower than a predetermined factor defined by a predetermined threshold value. For example, the difference in pixels brightness (i.e. brightness level measured as a pixel gray level) may be defined by factor of 2. Generally, the difference factor depends on many aspects of the imaging being used, such as optics, CCD integration time, etc.

The present invention utilizes a dark-field imaging technique. This is based on the inventors' understanding of the following: Due to the high aspect ratio of the via geometry (long and narrow via), the via acts as extremely efficient scatterer for incident radiation.

It should be noted that for the purposes of the present disclosure, the term "scattering" signifies a radiation response to incident radiation with one or more parameters essentially different than corresponding one or more parameters of the incident radiation. The term "image" refers to a picture of the pattern. The term "brightness" signifies a pixels brightness level (corresponding to a detected signal intensity level) typically measured as a pixel gray level.

This approach enables to identify via(s) in a dark-field image of the sample (e.g. selected site). In this connection, it should be understood that the term "dark-field image" signifies image formed by collection/detection of a radiation response with collection/detection conditions different from those of illumination. Typically, dark field imaging mode/scheme can be provided by collecting light propagating in directions different from that of specular reflected light, and/or collecting light of polarization state(s) different from that of the illumination.

Generally, such radiation parameter(s) in which the radiation response is different from the incident radiation includes direction of propagation and/or polarization state. For example, radiation (light) incident on the via at some specific direction and polarization, is reflected from the via (generally, returns from the via) in a (broad) range of directions and polarizations.

FIG. 1C illustrates angular distribution of the reflected intensity from a 4 µm diameter, 40 µm deep TSV, obtained using normal incidence mode. The TSV acts as an efficient scatterer, leading to strong non-specular scattering, and consequently strong dark-field signal.

Thus, generally, using a dark-field imaging scheme, provides that vias appear in the image as bright regions on a dark background, the background corresponding to a relatively planar surface of the structure/wafer, as well as a periodic pattern in between the vias, which mainly respond by specular reflection and/or the same polarization as the illumination. Moreover, the high aspect ratio via significantly affects (mixes/rotates) polarization of light interacting therewith, and accordingly, by using polarization-based dark-field imaging scheme, the vias appear in the image as bright regions on a dark background with a higher contrast. Such polarization-based dark-field imaging scheme can be provided using, for example, polarizer and analyzer with mutually orthogonal polarization axes in the illumination and detection channels respectively.

According to the invention, the existence of a defect inside the via is detected by its effect on the intensity of light returned from the via. In this connection, the inventors have found that although the defect, similar to the via itself, commonly acts as an efficient dark-field scatterer, this defect-originated scattering is negligible as compared to the strong dark-field scattering signal originating from the via itself. However, the defect also acts as a relatively strong light absorber, and this effect leads to significant decrease in the measured dark-field scattering signal from the via with a defect (defective via), as compared to that of the normal via. As a result, in the dark-field image obtained with a field of view covering several vias (generally, at least two vias), normal and defective vias appear with first and second brightness respectively on the relatively dark background, where the first and second brightness are characterized by relatively higher and lower intensities (by a predetermined factor, e.g. factor of 2 and higher).

The above technique enables fast and effective inspection of patterned structures by imaging them (e.g. while scanning) using dark-field imaging scheme as defined above, analyzing the image to identify (and possibly also locate) defective vias, and generating corresponding inspection data. The inspection data may be used for sorting the structures, and possibly transferring the potentially defective structures (those with the identified defective vias) for further verification. Such verification may be performed using any suitable imaging and/or metrology equipments, such as SEM or OCD technique, or a combination of both, for example as described in WO 13/121423 and U.S. Pat. No. 8,848,185, both assigned to the assignee of the present application and incorporated herein by reference.

Thus according to a broad aspect of the invention, there is provided a method for inspecting patterned structures for detecting defective features of a pattern, where the features under inspection are narrow grooves having high aspect ratio geometry, the method comprising:

dark-field imaging of at least a region of the structure including a plurality of the grooves; and generating data indicative of a dark-field image of said at least region of the structure;

processing said data indicative of the dark-field image, said processing comprising analyzing pixels brightness within the image, and upon identifying a condition that brightness of the pixels corresponding to at least one of said grooves in said dark-field image is lower than nominal brightness by a predetermined factor, generating output data indicative of existence of at least one defective groove in said at least region of the structure.

The nominal brightness may be that of other similar features in the captured dark-field image (e.g. average brightness) and/or the brightness of the corresponding feature in a reference (golden) dark-field image.

In some embodiments, the processing further comprises determining location data for the at least one defective feature.

In some embodiments, the imaging further comprises applying a bright field imaging scheme to the same region/site of the structure, and capturing bright-field image. The analyzing of the pixels brightness for the dark-field image may further comprise comparing the dark-field image with the bright-field image.

In some embodiments, the method further comprises utilizing the output data indicative of the at least one defective groove, for classifying the corresponding structure as a defective structure, and generating corresponding classification data. The classification data, preferably together with the location data for each defective feature, may be used for further inspection/verification and sorting.

In some embodiments, the dark-field imaging scheme is a cross-polarization scheme. In some embodiments, such cross-polarization scheme is used in the normal incidence measurement scheme.

The features being inspected are elongated grooves with a high aspect ratio, i.e. a ratio between the groove length to groove lateral dimension(s) of at least 6. These may be vias in a semiconductor wafer.

According to another broad aspect, there is provided a method for inspecting semiconductor wafers comprising narrow vias having high aspect ratio geometry for detecting defective vias in the wafer, the method comprising:

dark-field imaging of at least a region of the wafer including a plurality of the vias; and generating data indicative of a dark-field image of said at least region of the wafer;

processing said data indicative of the dark-field image, said processing comprising analyzing pixels brightness within the image, and upon identifying a condition that brightness of the pixels corresponding to at least one of said vias in said dark-field image is lower than nominal brightness by a predetermined factor, generating output data indicative of existence of at least one defective via in said at least region of the wafer.

The dark-field imaging may be performed with a field of view of the imaging system covering a portion of the pattern including several grooves (vias). The inspection may be performed using scanning of the structure, or is applied to one or more selected sites of the structure.

According to yet further aspect of the invention, it provides an inspection system for inspecting structures having a pattern formed by an array of narrow grooves having high aspect ratio geometry for detecting defective grooves, the system comprising:

an imaging system configured and operable for imaging the structure by applying a dark-field imaging scheme to at least a region of the structure comprising a plurality of the grooves, and generating data indicative of a dark-field image of said at least region of the structure;

a control unit configured for data communication with the imaging system, the control unit comprising an analyzer module configured for analyzing pixels brightness within said data indicative of the dark-field image, and upon identifying a condition that brightness of the pixels corresponding to at least one of said grooves in said dark-field image is lower than nominal brightness by a predetermined factor, generating output data indicative of existence of at least one defective groove in said at least region of the structure.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A and 1B exemplify possible defects inside the vias, where FIG. 1A exemplifies sharp spikes at the bottom of via or on the via wall, and FIG. 1B exemplifies a defect in the form of a non-etched portion of the via wall;

FIG. 1C shows angular distribution of reflected light from a TSV, illuminated at normal incidence;

FIG. 3A illustrates the image of the illuminated spot on the wafer obtained using a bright-field imaging, FIG. 3B is the image obtained from the wafer when imaging in an angular dark-field scheme, and FIG. 3C illustrates a dark-field image of the illumination spot of the wafer obtained using the cross-polarization scheme.

DETAILED DESCRIPTION OF EMBODIMENTS

The present invention provides an inspection technique for identifying defects in groove-features of the surface pattern of a structure, such as vias in semiconductor wafers. FIGS. 1A and 1B exemplify possible defects inside the vias, such as sharp spikes at the bottom of via or on the via wall, and a non-etched portion of the via wall.

Figure 2:
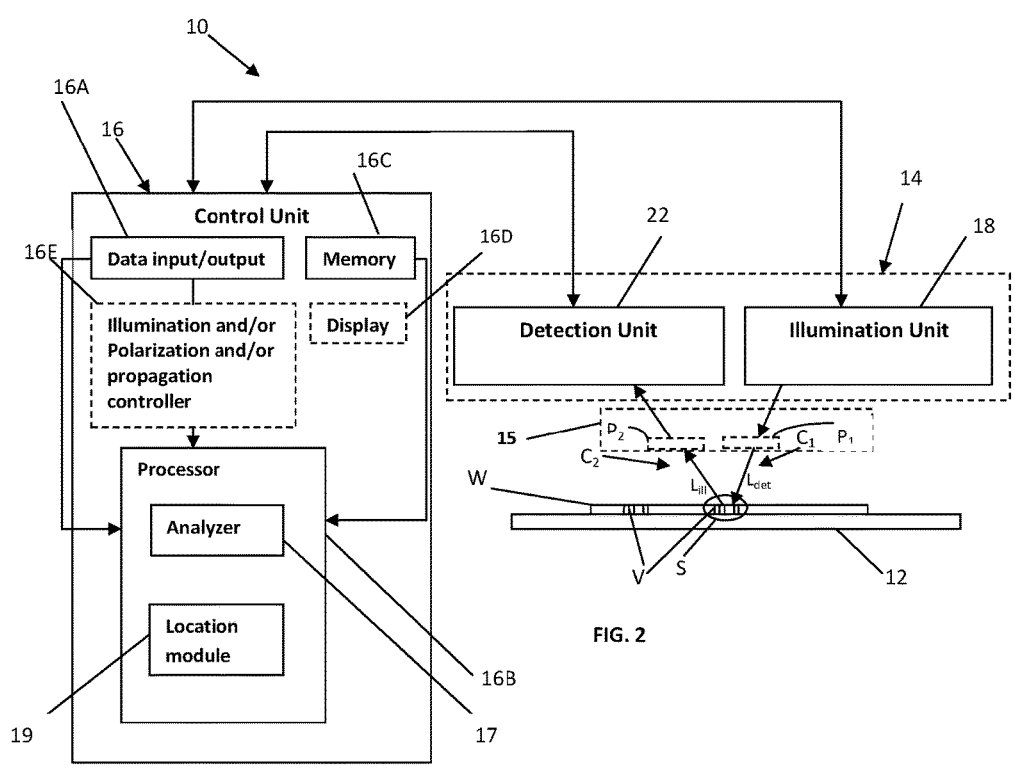
FIG. 2 is a block diagram of an example of the inspection system of the invention illustrating schematically the configuration of an imaging system and a control unit.

Reference is made to FIG. 2 showing schematically, by way of a block diagram, an inspection system 10 of the present invention for automatic inspecting of a patterned structure (e.g. wafer) for defects, especially defects inside the grooves, i.e. surface relief/pattern of the structure. The inspection system 10 includes an imaging system 14 for imaging a structure (wafer) W while located on a support stage 12; and a control unit 16. The imaging system 14 is configured to perform dark-field imaging scheme(s) on at least a region of the wafer including a plurality of the grooves, and providing an image (picture) of the structure (at least a region thereof). It should be noted that the imaging may utilize scanning of the structure, or imaging one or more selected sites (regions of interest) on the structure. The imaging system is preferably configured with a field of view selected to "cover" (image) the plurality of grooves.

The control unit 16 is connectable (via wires or wireless signal transmission) to the output of the imaging system 14, and configured for processing the captured dark-field image, as well as operating/managing the operation of the imaging system. This will be described more specifically further below.

The imaging system 14 includes an illumination unit 18 and a detection unit 22, and defines illumination and detection channels $C_1$ and $C_2$ configured for the system operation in the dark-field imaging mode. The radiation source of the illumination unit 18 may be a broadband source producing a light beam of multiple wavelengths, or a narrowband source. The detection unit 22 is configured for receiving radiation returning from an illuminated spot S and generating image thereof.

As said, the imaging system 14 is capable of imaging a structure having a pattern formed by a plurality of spaced apart elongated (high aspect ratio) grooves, e.g. vias, V, and possibly also including some periodic pattern on top of the structure. The imaging is performed using a relatively large field of view such that the image is a picture of a portion of the pattern including a plurality of vias V. The control unit performs image processing of the detected image to identify defective via(s). The imaged region of the structure may for example have a dimension about 1 mm, while the via has typically a diameter (lateral dimension) of a few microns (FIG. 1C exemplifies the case of 4 microns diameter via) and the vias are typically spaced by a distance larger than the via's dimension, e.g. larger by a factor of 2. This functionality of the system allows for using it in automatic (on-line) inspection of structures progressing on a production line, i.e. during the manufacturing process, e.g. patterning process.

As also indicated above, the imaging system 14 is configured for dark-field inspection/imaging mode. As will be described below, such dark-field inspection mode may be implemented using one or more suitable schemes. Generally, the dark field imaging is performed by proper configuration of the detection channel with respect to the illumination channel, such that detected light is different from the illuminating light in at least one property including one or more of the following: polarization state, direction of propagation, etc.

It should be noted that the dark-field mode is commonly referred to as the mode utilizing detection of light formed by light propagating from the structure in directions other than that of specular reflection of illumination. This does not necessarily mean that the detection channel is oriented outside the specular reflection propagation zone. In fact, the detection channel may be equipped with a filter/mask that blocks the specular reflection (bright-field detection channel). Another example of a dark field mode is by utilizing a polarization filter including a filter unit at least in the detection channel and configured for blocking light with the polarization state of the illuminating light.

Generally, there are various optical dark-field schemes, including for example the following schemes: dark field setup configured for affecting polarization of light propagating in illumination and detection channels; dark field detection mode achieved by affecting propagation of light through the illumination and detection channels, using a common pattern (light-path masks) in the illumination and detection channels, e.g. complementary masks in the illumination and collection channels; dark field detection mode achieved by spatially separating the illumination and detection channels by using different azimuth and elevation for the illumination and detection channels. Various system configurations utilizing these dark-field schemes are described for example in U.S. Pat. No. 8,848,185 assigned to the assignee of the present application and are incorporated herein by reference.

As indicated above, the present invention utilizes any one or more of the known dark-field inspection schemes, for detecting "scattering" from the illuminated structure, namely a radiation response to incident radiation with one or more parameters essentially different than corresponding one or more parameters of the incident radiation.

In the present not limiting example of FIG. 2, the imaging system 14 is configured for performing polarization-based dark-field imaging scheme. To this end, the imaging system 14 includes a polarization assembly 15. The polarization assembly 15 may be associated only with the detection channel $C_2$, namely may include only a polarizer $P_2$ located in the detection channel, in case the illumination unit produces illuminating light of a specific polarization. Alternatively (or additionally), as shown in the present example of FIG. 2, the polarization assembly 15 may be configured for operating with cross-polarization scheme, namely includes two polarizers $P_1$ and $P_2$ in the illumination and detection channels, respectively, having orthogonal orientations of their preferred polarization planes, such that polarizer $P_2$ blocks light having the polarization state of the illumination, e.g. light propagating to the structure via the polarizer $P_1$ and allows detection only of scattered light $L_{scat}$ having orthogonal polarization.

Also, in the present example, the imaging system is illustrated as operating with oblique illumination. It should, however, be understood that the imaging technique of the invention is limited neither to specific incidence configuration (oblique or normal) nor to the use of any specific dark-field scheme, e.g., polarization scheme such as cross polarization. The imaging system 14 is configured to perform dark-field imaging mode(s) enabling imaging of vias as bright features on dark background (surface of the structure). As described above, and will be exemplified further below, the defective vias affect the amount of scattered light and accordingly they would appear in the image with less brightness as compared to the normal vias (by a predetermined factor).

Generally, by using dark-field modes, a detection channel is configured to collect light having properties different from those of the illumination, e.g. propagating outside the specular reflection path (e.g. by using masking of the detection and possibly also illumination channels) and/or having polarization state orthogonal to that of the illumination. In some embodiments, the imaging system may also be operable in bright-field imaging mode. This can be achieved by using an additional bright-field detection channel, or by selectively shifting the mask(s) as well as polarizer(s) to be in and out of the light propagation channel(s), thus selectively operating the system in rather bright or dark field modes, rather than using separate illumination and/or detection channels for the dark- and bright-field operational modes. As will be exemplified below, the bright-field image can be used for image registration, and the dark-field image can then be used to identify the defective vias.

As stated above, different dark-field imaging schemes can be used for imaging and defect detection. FIG. 2 illustrates a specific but not limiting example, utilizing the so-called cross-polarization scheme, according to which illuminated light $L_{ill}$ is set to some polarization by either utilizing polarized illumination unit or providing a polarizer $P_1$ in the illumination propagation path $C_1$, and a corresponding analyzer $P_2$ is provided in the detection channel $C_2$. Thus, the polarized light $L_{ill}$ is blocked in the return path by polarizer/analyzer $P_2$, whose preferred polarization plane is oriented orthogonally to that of the polarized light $L_{ill}$. By this, detected light $L_{det}$ includes essentially light returned from "scatterers" (polarization rotators) features of the structure, while light returned from features of the structure which do not affect (rotate) polarization is substantially prevented from reaching the detector. It should be understood, and also described above with reference to U.S. Pat. No. 8,848,185 assigned to the assignee of the present application, polarizer $P_2$ may include a phase retarder; or the polarizer assembly 15 may include a common polarizer accommodated in the overlapping region of the illumination and detection channels, as the case may. As vias (narrow elongated grooves) cause extremely efficient polarization rotation, the use of cross-polarization scheme for imaging, provides that vias would appear bright on dark background.

Considering another possible dark-field imaging scheme, illuminating light may be incident on the structure with some angular distribution, and collected at some different angular distribution which has no overlap with the illumination. In this method, all specular reflections would not reach the detector. However, the vias, being strong non-specular reflecting elements, would contribute strong signal.

The expected performance from different dark-field imaging schemes, namely a difference in the detected intensities from the normal and defective vias, depends inter alia on the via dimensions and the defect structure. The dark-field imaging scheme is properly selected to provide that scattering from the via surroundings (i.e. from the substantially planar surface regions and from other periodic patterns) is relatively weak. For example, if the via is embedded in a region where a periodic grating structure is printed on the wafer top, cross-polarization scheme can be used, where the illuminated polarization is oriented in one of the major axes of the grating, so that the grating itself does not contribute any cross-polarization signal, providing good contrast for the via. It is furthermore possible to use several dark-field imaging schemes consecutively, to obtain more information on the defect, as well as improved sensitivity and more robust defect identification.

Figure 3A:
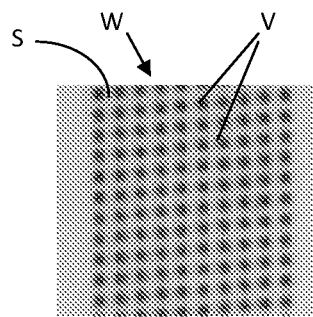
FIGS. 3A to 3C show three examples of images of a wafer containing a patterned structure of spaced-apart vias, where
Figure 3B:
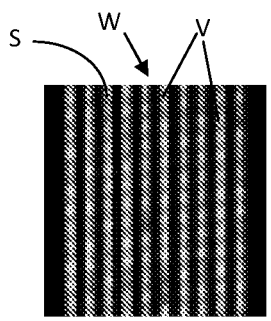
Figure 3C:
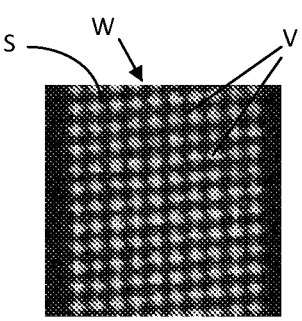

Referring to FIGS. 3A-3C, there are shown three examples of images of a wafer containing a patterned structure of spaced-apart vias.

FIG. 3A illustrates the image of the region of wafer captured using a bright-field imaging scheme. In this image, vias V are shown as dark spots on a bright background which is the wafer's surface. This is because the vias scatter the light and deviate the illumination from the specular direction, or, in case the illuminating light is polarized, the vias rotate the original polarization of the illuminating light. Accordingly, the signals from the vias reaching the detectors are relatively weak as compared to the signals from wafer's surface which substantially does not affect the polarization. Vias are "dark" relative to the background because they almost do not return reflected light (specular reflection), and at the same time provide sufficiently weak scattered signal.

FIG. 3B is the image obtained from the wafer when imaging in an angular dark-field scheme described above, namely detecting light with angular propagation different than that of the specular reflection. As the vias are strong non-specular reflecting elements, the vias V appear bright in the dark-field image, as the specular reflection is prevented from reaching the detection unit. However, as seen in the figure, the resolution obtained with this dark-field scheme might not be sufficiently high. This is because a via has a lot of interfaces that differently reflect incident light and thus cause the returned light to propagate from multiple interfaces in multiple directions.

FIG. 3C illustrates a dark-field image of the wafer obtained using the cross-polarization scheme described above with reference to FIG. 2. As appreciated, the vias V appear as bright circles on a dark background, because they "spoil" the polarization state of the illumination and return other polarizations which can be detected by imaging with a dark-field mode.

Figure 4A:
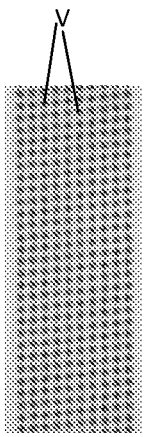
FIGS. 4A and 4B are the experimental results, showing the bright-field image and the dark-field image of the same measurement spot of the wafer, for the wafer containing defective vias.
Figure 4B:
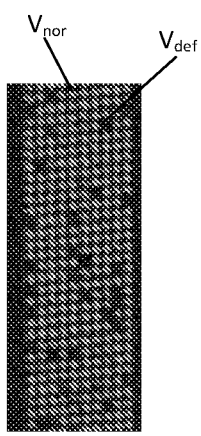

Reference is made to FIGS. 4A and 4B showing the experimental results comparing the imaging technique of the invention (FIG. 4B) with the typical bright-field imaging scheme (FIG. 4A), applied to the same region/site of the structure. In this experiment, the fabrication process parameters were intentionally tuned to create a high probability of defected vias. In the example of FIG. 4B, the wafer was imaged with the dark-field imaging mode, using the cross-polarization scheme of FIG. 2.

As shown, in both images of FIGS. 4A and 4B, vias can generally be identified. In FIG. 4A presenting a bright-field image, the array of vias V appears regular and uniform, with no difference observed between the vias. However, FIG. 4B demonstrating the image obtained using a dark-field imaging technique, provides clear identification of several abnormal (defective) vias $V_{def}$ appearing as dark regions among the bright normal vias $V_{nor}$.

In this connection, reference is made back to FIG. 2, illustrating schematically the configuration of the control unit 16 which processes data indicative of the dark-field image of the plurality of grooves, generated by the imaging system 14 (detection unit 22). It should be noted that the control unit may receive such data directly from the detection unit 22 during the inspection session (on-line inspection mode), or may generally receive this data from a storage utility in which such data have been previously stored (off-line mode).

The control unit 16 is typically a computer system having data input/output utilities 16A, data processor and analyzer module 16B, memory 16C, and possibly also a display 16D. The control system may also include various controllers, generally at 16E, for example for controlling the illumination, as well as for controlling the dark-field mode conditions such as polarization and/or masking of either one or both of the illumination and detection channels and/or the orientation of the detection channel relative to the illumination channel. For example, the controller 16E is configured for controlling the elements and parameters of the cross-polarization scheme, i.e. the polarizers $P_1$ and $P_2$. It should also be noted that the polarizer(s) $P_1$ and/or $P_2$ may be integrated in the illumination unit and/or the detection unit respectively.

The control system 16 (its data input utility 16A) receives data indicative of the dark-field image detected by the imaging system 14 (either from the detection unit 22, or generally from any storage device). This image data (gray level pixels' data) is processed by the data processor and analyzer 16B, which operates to identify existence of defective via(s) in the image data and generate corresponding output data. The data processor and analyzer utility may also be configured for providing location data for the defective vias. The defect detection may be performed by applying to the image raw data any known suitable image processing technique utilizing pattern recognition approach.

For example, the data processor 16B may include an analyzer module 17 configured (preprogrammed) for analyzing pixels brightness in the dark-field image and applying comparison algorithm(s). This includes comparison of the pixels brightness in the detected dark-field image data with nominal brightness data. The nominal brightness data corresponds to pixels brightness of a normal (non-defective) grooves. This may include the brightness data of a reference dark field image (golden image) of a similar structure with no defective vias (the reference image data may be stored in the memory 16C or received from a server utility via a communication network, as the case may be); or the brightness data of pixels corresponding to the other vias in the structure under inspection. Additionally or alternatively, the analyzer module 17 may apply a comparison algorithm for comparing the received data indicative of the dark-field image of the wafer with a bright-field image of the same region/site of the structure. Thus, the analyzer module detects and analyzes the brightness of pixels corresponding to vias in the dark-field image (light response intensities) as compared to nominal brightness, and generates data indicative thereof. The deviation of the detected pixels brightness from the nominal brightness can for example be determined based on a predetermined intensity threshold: in a dark-field image, light returned from the defective vias has lower intensity than the nominal value by a predetermined factor (darker image) as compared to the non-defective vias. Also, in order to distinguish between the dark regions corresponding to the surface between the vias and the dark regions corresponding to the defective vias, either reference data (vias' map) or a thresholding technique, can be used.

The so-obtained data indicative of the existence of defective vias can be directly used for classifying the respective wafers as defective ones and thus enabling to apply appropriate sorting technique (e.g. at a downstream sorting station of the production line) to remove the respective wafers from the production line or to transfer them to a verification station. In some embodiments, this data indicative of the existence of defective via(s) is further processed by a location module 19, which utilizes the map of inspected region(s) and assigns location data to the sites containing defective vias, i.e. "virtually marks" the sites containing abnormal/defective vias to be used in further verification. The wafers with the corresponding assigned location data for the defective vias can be then used at the verification station to guide the verification inspection to the specific sites in the wafer.

As indicated above, the imaging system 14 can be switchable between the bright-field and dark-field operational modes, or the system 14 may include two respective subsystems (e.g. using common illumination or detection channels). As shown in FIG. 4A, the bright-field image is insensitive to the existence of defective vias, and can thus be used for image registration, while the dark-field image, which is highly sensitive for defective vias is then used to identify (and possibly also locate) the defective vias.

The control unit 16 may be configured to generate output data indicative of existence of defective vias in a specific wafer and display a map/distribution of the defective vias alone, appearing as bright (lit) circles on a dark background, where each circle has its location data (e.g. in a Cartesian coordinate system). Alternatively the control unit may display all the vias, a non-defective as bright circles and the defective ones as dark circles or as voids among the bright circles of the non-defective vias.

It should be noted that the defect identification as described above (by the control unit 16) can be used in conjunction with other via defect inspection techniques. For example, the high throughput allowed by this method (automatic inspection), where a large field of view can be instantly analyzed, can be used to highlight suspected vias which will then be analyzed (verified) using a second (slower) method. One such second method is described in the above-mentioned WO 2014/006614 assigned to the assignee of the present invention, which is incorporated herein by reference.

Thus, the present invention provides a simple and effective technique for highly reliable identification of defective vias/grooves in patterned structures, while imaging the structure using dark-field imaging scheme to obtain dark-field images (pictures) of multi-vias containing regions. This technique is particularly useful for automatic inspection of structures, e.g. progressing on the production line.

The invention claimed is:

1. A method for inspecting patterned structures for detecting defective features of a pattern, where the features under inspection are narrow grooves having high aspect ratio geometry, the method comprising:
performing dark-field imaging of at least a region of the structure including a plurality of the grooves, said dark-field imaging comprising illuminating said at least region of the structure including the plurality of the grooves according to a predetermined dark-field imaging scheme and detecting light returned from inside of the grooves in said region; and generating data indicative of a dark-field image of said at least region of the structure;
processing said data indicative of the dark-field image, said processing comprising analyzing pixels brightness within the image, and upon identifying a condition that brightness of the pixels corresponding to at least one of said grooves in said dark-field image is lower than nominal brightness by a predetermined factor, generating output data indicative of existence of at least one defective groove in said at least region of the structure.

2. The method according to claim 1, wherein said imaging is performed with a field of view selected such that the image includes a portion of the pattern including the plurality of the grooves.

3. The method according to claim 1, wherein the nominal brightness is defined by at least one of the following: (i) brightness of pixels in said dark-field image corresponding to other grooves in said pattern; and (ii) brightness of pixels corresponding to grooves in a reference dark-field image.

4. The method according to claim 1, wherein said processing further comprises determining location data for said at least one defective groove.

5. The method according to claim 4, wherein said analyzing of the pixels brightness further comprises comparing the dark-field image with the bright-field image.

6. The method according to claim 1, wherein said imaging further comprises applying a bright field imaging scheme to said at least region of the structure, and generating a bright-field image.

7. The method according to claim 1, wherein said analyzing of the pixels brightness comprises comparing said data indicative of the dark-field image to a reference dark-field image.

8. The method according to claim 1, further comprising at least one of the following: (a) utilizing said output data indicative of said at least one defective groove, classifying the corresponding structure as a defective structure, and generating classification data; and (b) inspecting at least one site of the structure including said at least one defective groove.

9. The method according to claim 1, further comprising utilizing said output data indicative of said at least one defective groove, classifying the corresponding structure as a defective structure, generating classification data, and storing the classification data.

10. The method according to claim 1, wherein said predetermined dark-field imaging scheme comprises illuminating the structure with normal incidence mode.

11. The method according to claim 10, wherein the predetermined dark-field imaging scheme further comprises a cross-polarization scheme.

12. The method according to claim 1, wherein the structure is a semiconductor wafer formed with the pattern of vias.

13. The system according to claim 1, wherein said imaging system is further configured for performing a bright field imaging scheme for said at least region of the structure, and, generating a bright-field image, said analyzer module being configured for analyzing the pixels brightness by comparing the dark-field image with the bright-field image.

14. The method according to claim 1, wherein the geometry of the grooves has the high aspect ratio of at least 6.

15. The method according to claim 1, wherein the predetermined dark-field imaging scheme comprises a cross-polarization scheme.

16. A method for inspecting patterned structures comprising narrow grooves having high aspect ratio geometry for detecting defective grooves in the patterned structure, the method comprising:
imaging at least a region of the structure, said imaging comprising performing at least dark-field imaging said at least region of the structure including a plurality of the grooves having high aspect ratio geometry with a dark-field imaging scheme comprising illumination of said at least region of the structure with normal incidence mode to detect light returned from inside of the grooves in said region, and generating data indicative of a dark-field image of said at least region of the structure;

processing said data indicative of the dark-field image, said processing comprising analyzing pixels brightness within the image, and upon identifying a condition that brightness of the pixels corresponding to at least one of said grooves in said dark-field image is lower than nominal brightness by a predetermined factor, generating output data indicative of existence of at least one defective groove in said at least region of the structure.

17. The method according to claim 16, wherein the geometry of the grooves has the high aspect ratio of at least 6.

18. The method according to claim 16, wherein the predetermined dark-field imaging scheme further comprises a cross-polarization scheme.

19. The method according to claim 16, wherein the structure is a semiconductor wafer formed with the pattern of grooves.

20. An inspection system for inspecting structures having a pattern formed by an array of narrow grooves having high aspect ratio geometry for detecting defective grooves, the system comprising:

an imaging system configured and operable for imaging the structure by applying a dark-field imaging scheme to at least a region of the structure comprising a plurality of the grooves by illuminating said at least region and detecting light returned from inside of the grooves, and generating data indicative of a dark-field image of said at least region of the structure;

a control unit configured for data communication with the imaging system to receive said data indicative of the dark-field image of said at least region of the structure, the control unit comprising a data processor configured to process the dark-field image to identify one or more defective groves among the one or more of the narrow grooves in said at least region of the structure being imaged, the data processor comprising an analyzer module configured to analyze pixels brightness within said data indicative of the dark-field image, and upon identifying a condition that brightness of the pixels corresponding to at least one of said grooves in said dark-field image is lower than nominal brightness by a predetermined factor, generating output data indicative of existence of at least one defective groove in said at least region of the structure.

21. The system according to claim 20, wherein said imaging system comprises a polarization unit configured and operable with a cross-polarization scheme; said imaging system is configured to perform said dark-field imaging scheme using normal incidence mode.

22. The system according to claim 20, wherein the nominal brightness is defined by at least one of the following: the nominal brightness is defined by brightness of pixels in said dark-field image corresponding to other grooves in said pattern; and the nominal image brightness is defined by brightness of pixels corresponding to grooves in a reference dark-field image.

23. The system according to claim 20, wherein said control unit is configured to carry out at least one of the following: determining location data for said at least one defective feature; and utilizing said output data indicative of said at least one defective groove, for classifying the corresponding structure as a defective structure, and generating classification data.

24. The system according to claim 20, wherein said analyzer module is configured for comparing the dark-field image to a reference dark-field image having no defective grooves.

25. The system according to claim 20, wherein said imaging system has at least one of the following configurations: said imaging system is operable with a field of view selected such that the dark-field image includes a portion of the pattern including a plurality of said features; said imaging system comprises a polarization unit configured and operable with a cross-polarization scheme; said imaging system is configured for performing a bright field imaging scheme for said at least region of the structure, and generating a bright-field image.

* * * * *